(12) United States Patent
Yang et al.

(10) Patent No.: US 11,246,514 B2
(45) Date of Patent: Feb. 15, 2022

(54) NON-INVASIVE OPTICAL INTERNAL SUBSTANCE DETECTOR

(71) Applicants: HYUNDAI MOTOR COMPANY, Seoul (KR); KIA MOTORS CORPORATION, Seoul (KR)

(72) Inventors: Sang Hyeok Yang, Suwon-si (KR); Dong Gu Kim, Hwaseong-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 349 days.

(21) Appl. No.: 16/425,277

(22) Filed: May 29, 2019

(65) Prior Publication Data
US 2020/0245906 A1 Aug. 6, 2020

(30) Foreign Application Priority Data
Feb. 1, 2019 (KR) .......................... 10-2019-0013950

(51) Int. Cl.
| | |
|---|---|
| *A61B 5/1455* | (2006.01) |
| *G02B 3/00* | (2006.01) |
| *A61B 5/00* | (2006.01) |
| *A61B 5/145* | (2006.01) |

(52) U.S. Cl.
CPC ........ *A61B 5/1455* (2013.01); *A61B 5/14532* (2013.01); *A61B 5/4845* (2013.01); *G02B 3/0006* (2013.01); *A61B 2562/0238* (2013.01)

(58) Field of Classification Search
CPC . A61B 5/0205; A61B 5/1455; A61B 5/14551; A61B 5/14552; A61B 5/14532; A61B 5/4845; A61B 2562/0238; A61B 2562/046; A61B 5/02427; A61B 5/0059; A61B 5/145
See application file for complete search history.

(56) References Cited

U.S. PATENT DOCUMENTS

| | | | | |
|---|---|---|---|---|
| 6,119,031 | A * | 9/2000 | Crowley | A61B 5/0075 600/310 |
| 8,452,402 | B2 * | 5/2013 | Ecker | A61B 5/0086 607/23 |
| 8,581,697 | B2 | 11/2013 | Ridder et al. | |
| 2007/0100219 | A1 * | 5/2007 | Sweitzer | A61B 5/14551 600/323 |
| 2008/0208018 | A1 | 8/2008 | Ridder et al. | |
| 2010/0241006 | A1 * | 9/2010 | Choi | A61B 5/14553 600/476 |
| 2013/0317328 | A1 | 11/2013 | Ridder et al. | |
| 2019/0387972 | A1 * | 12/2019 | Hu | A61B 5/14552 |

* cited by examiner

*Primary Examiner* — Chu Chuan Liu
(74) *Attorney, Agent, or Firm* — Lempia Summerfield Katz LLC (57) ABSTRACT

A non-invasive optical internal substance detector includes: a diode array including a plurality of light emitting diodes (LEDs) for emitting light toward a target where an internal substance is detected, and a plurality of photodiodes (PDs) for receiving light which is reflected from the target after being emitted from the plurality of light emitting diodes; and a controller for controlling the plurality of light emitting diodes to be turned on or off and for processing a signal obtained from the photodiodes. The plurality of light emitting diodes and the plurality of photodiodes each have a size of several micrometers to several tens of micrometers and are arranged at intervals of several micrometers to several tens of micrometers from each other.

11 Claims, 5 Drawing Sheets

NON-INVASIVE OPTICAL INTERNAL SUBSTANCE DETECTOR

CROSS-REFERENCE TO RELATED APPLICATION

This application claims priority to and the benefit of Korean Patent Application No. 10-2019-0013950, filed on Feb. 1, 2019, the entire contents of which are incorporated herein by reference.

FIELD

The present disclosure relates to a non-invasive optical internal substance detector.

BACKGROUND

The statements in this section merely provide background information related to the present disclosure and may not constitute prior art.

Conventionally, various attempts have been made to non-invasively detect an alcohol concentration of a living tissue. Systems for the non-invasive detection have also been constructed using polarimetry, mid-infrared spectroscopy, Raman spectroscopy, kormoscopy, and radio-frequency spectroscopy. The above-described method is referred to as an optical measurement method.

In recent years, attempts have been made to prevent drunk driving with an alcohol detecting sensor installed inside a vehicle so as not to start an engine when a driver of the vehicle is drunk. An optical alcohol detector using the above-described optical measurement method may be considered as the alcohol detecting sensor applicable to the vehicle.

Meanwhile, a breath measurement method may be considered as a method for measuring the alcohol concentration in the body, in addition to the above-described optical measurement method. However, in the case of a breath measurement method, there is a problem that any person who is not drunk starts the engine and a drunk driver may take over the vehicle. Compared to this, because the optical alcohol detector is easily integrate with a driver's recognition function of the vehicle, preventing starting of the engine by a drunk driver may be effectively preformed.

However, we have discovered that a conventional optical alcohol measuring device including a light emitter, a light receiver, and a circuit for processing signals of the light emitter and the light receiver is too large to be applied to a target device of the vehicle such as a start button. Thus, it is desired to downsize the optical alcohol measuring device having a size enough to be installed in a place such as a start button that provides lock function of starting the engine.

SUMMARY

The present disclosure has been made to solve the above-mentioned problems occurring in the prior art while advantages achieved by the prior art are maintained intact.

An aspect of the present disclosure provides a miniaturized optical internal substance (e.g., alcohol) detector by integrating a configuration.

Also, an aspect of the present disclosure provides a structure for preventing an interference of components such as a light emitter and a light receiver due to the integration of the optical internal substance detector.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a non-invasive optical internal substance detector includes: a diode array which includes a plurality of light emitting diodes (LEDs) configured to emit light toward a target including an internal substance to be detected, and a plurality of photodiodes (PDs) configured to receive light reflected from the target after being emitted from the plurality of light emitting diodes; and a controller configured to control light emitting diodes of the plurality of light emitting diodes to be turned on or off and to process a signal obtained from the photodiodes.

In one form, the plurality of light emitting diodes and the plurality of photodiodes each have a size of several micrometers to several tens of micrometers and are arranged at intervals of several micrometers to several tens of micrometers from each other.

According to an aspect of the present disclosure, a non-invasive optical internal substance detector includes: a diode array in which a plurality of light emitting diodes (LEDs) for emitting light toward a target including an internal substance to be detected and a plurality of photodiodes (PDs) for receiving light which is reflected from the target after being emitted from the plurality of light emitting diodes are arranged at predetermined intervals, and a lens array disposed at one side of the diode array to converge the light emitted from the plurality of light emitting diodes and the light incident on the plurality of photodiodes.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

It should be noted that, in adding reference signs to the constituent elements in each of the drawings, the same constituent elements have the same reference signs even though they are illustrated in different figures. In addition, in the description of the present disclosure, when it is judged that detailed descriptions of known functions or structures may make the essential points vague, the detailed descriptions of the known functions or structures will be omitted.

Further, in the description of the constituent elements of the forms of the present disclosure, it is possible to use terms such as first, second, A, B, (a), (b) and the like. These terms are just to distinguish the constituent elements from any other constituent elements but do not limit the nature or sequence or order and the like of corresponding features by the terms. Additionally, it should be also understood that the expression that some constituent element is "connected", "coupled" or "joined" to another constituent element means that some constituent element may be directly connected or joined to another constituent element or is also "connected", "coupled" or "joined" to another constituent element through a further component therebetween.

Figure 1:
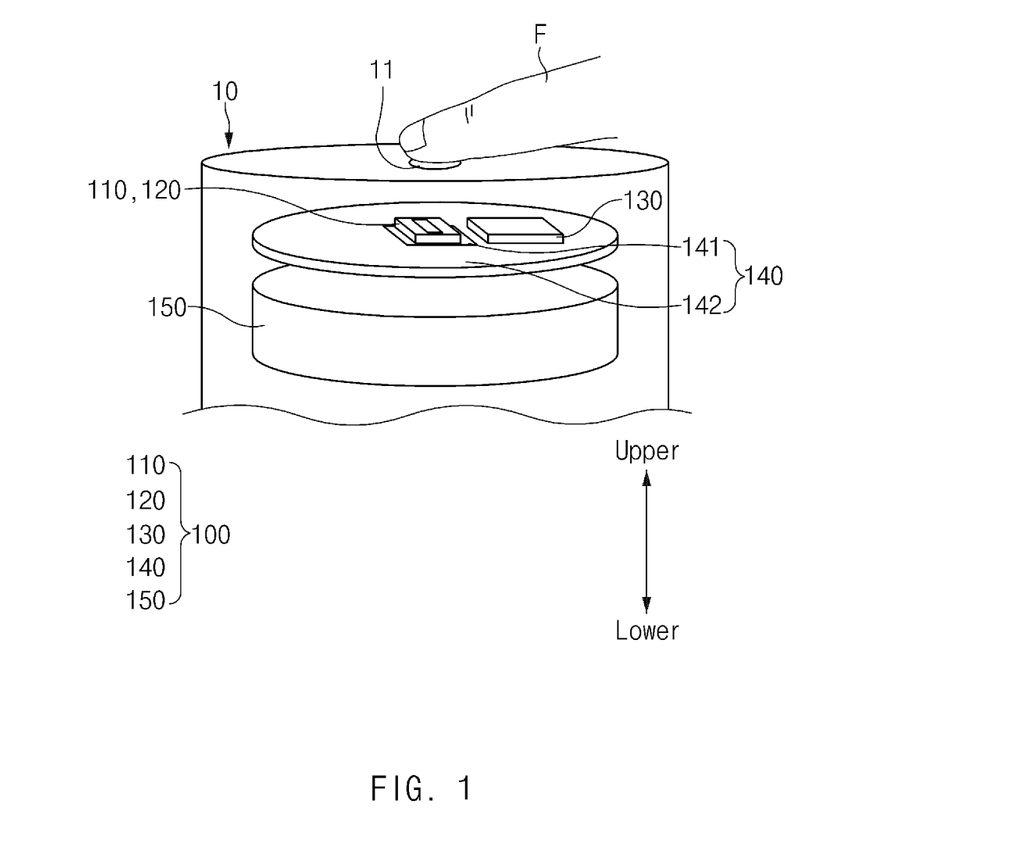
FIG. 1 schematically illustrates an optical alcohol detector installed on a button.
Figure 2:
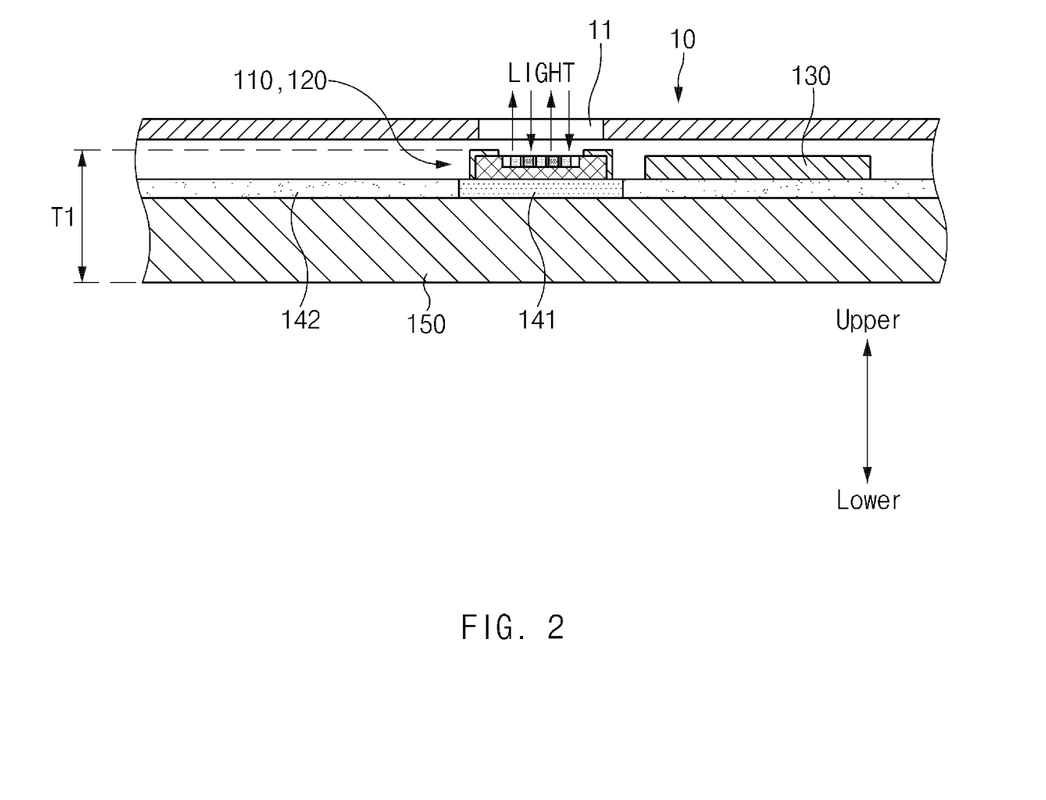
FIG. 2 is a vertical cross-sectional view illustrating a part of the button of FIG. 1.
Figure 3:
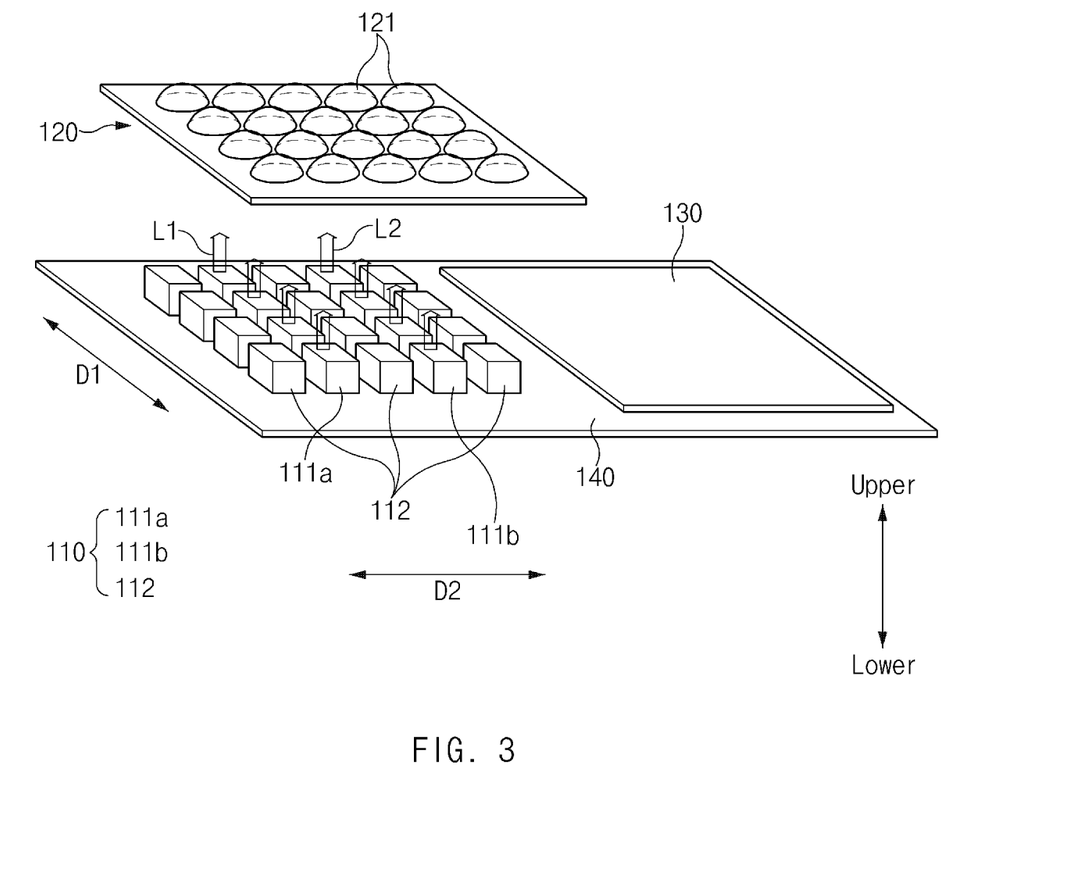
FIG. 3 schematically illustrates an optical alcohol detector.
Figure 4:
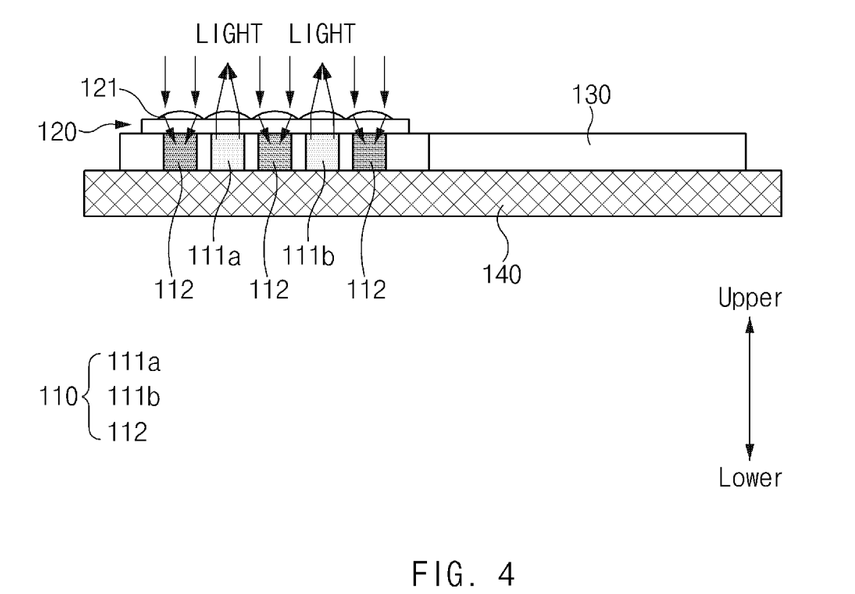
FIG. 4 is a vertical cross-sectional view illustrating the optical alcohol detector of FIG. 3.

FIG. 1 schematically illustrates an optical alcohol detector installed on a button in one form of the present disclosure, and FIG. 2 is a vertical cross-sectional view illustrating a part of the button of FIG. 1. FIG. 3 schematically illustrates an optical alcohol detector according to one form of the present disclosure, and FIG. 4 is a vertical cross-sectional view illustrating the optical alcohol detector of FIG. 3.

As one exemplary form of an optical internal substance detector, an optical alcohol detector 100 will be described. However, the scope of the present disclosure is not limited thereto. For example, the optical alcohol detector 100 may be used to detect glucose (blood glucose) in a body instead of alcohol through adjustment such as changing a wavelength of light.

In one form, the optical alcohol detector 100 includes a diode array 110 and a controller 130 for controlling the diode array 110.

The diode array 110 includes: a plurality of light emitting diodes (LEDs) 111a and 111b for emitting light toward a target F where alcohol is detected, and a plurality of photodiodes (PDs) 112 for receiving light, which is reflected from the target F after being emitted from the light emitting diodes 111a and 111b.

The target F may be an object to which the light emitted from the light emitting diodes 111a and 111b is reflected and may include alcohol. Referring to FIG. 1, for example, the target F may be a human finger. When a person consumes alcohol, a blood alcohol level becomes high, and the blood containing alcohol is introduced into the finger along a blood vessel.

In this case, the light absorption amount changes depending on the blood alcohol level when predetermined light (e.g., laser) is irradiated toward the finger. The blood alcohol level may be detected by examining the light reflected from the finger. The non-invasive optical alcohol detector of the present disclosure utilizes this principle.

Meanwhile, in one form, the controller 130 may be provided to control the plurality of light emitting diodes 111a and 111b to be turned on or off and to process a signal obtained from the photodiodes 112.

Conventionally, various attempts have been made to non-invasively detect an alcohol concentration of a living tissue. Systems for the non-invasive detection have also been constructed using polarimetry, mid-infrared spectroscopy, Raman spectroscopy, kormoscopy, and radio-frequency spectroscopy. The above-described method is referred to as an optical measurement method.

In recent years, attempts have been made to prevent drunk driving as an alcohol detecting sensor is installed inside a vehicle not to start an engine when be drunk. An optical alcohol detector using the above-described optical measurement method may be considered to be used as the alcohol detecting sensor applicable to the vehicle.

Meanwhile, a breath measurement method may be considered as a method for measuring the alcohol concentration in the body, in addition to the above-described optical measurement method. However, in the case of a breath measurement method, there is a problem that a nondrinking person starts the engine instead of a drinker. Compared to this, because the optical alcohol detector is easy to integrate with a driver recognition function of the vehicle, lock of starting the engine may be effectively realized.

However, we have found that a conventional optical alcohol measuring device including a light emitter, a light receiver, and a circuit for processing signals of the light emitter and the light receiver is too large to be applied to interior device of the vehicle. Especially, it is desired to downsize the optical alcohol measuring device having a size enough to be installed in a place such as a start button for applying to the driver lock function to prevent starting the engine.

Because the emitting diodes 111a and 111b in a micro unit, and the photodiodes 112 in a micro unit are integrated into a single chip, and the controller 130 is integrated into the same chip to provide a micro-alcohol sensor, the optical alcohol detector 100 is a microelectromechanical system (MEMS) chip capable of performing optical transmission, optical reception, and signal processing on one chip.

Features of the optical alcohol detector 100 according to one form will be described in detail below.

Referring to FIGS. 1 and 2, the optical alcohol detector 100 according to one form is installed in a button which a person touches, such as a start button 10 of a vehicle, thereby being arranged to detect alcohol when the person touches the button 10. To this end, a button window 11 may be formed on a surface of the button 10 which the person touches, light emitted from the optical alcohol detector 100 may be irradiated to the target F through the button window 11, and light reflected from the target F may be incident on the optical alcohol detector 100 through the button window 11.

The optical alcohol detector 100 may further include a lens array 120 disposed at one side of the diode array 110 to converge the light emitted from the plurality of light emitting diodes 111a and 111b and the light incident on the plurality of photodiodes 112.

The diode array 110 of the optical alcohol detector 100 includes the plurality of light emitting diodes 111a and 111b and the plurality of photodiodes 112. The plurality of light emitting diodes 111a and 111b and the plurality of photodiodes 112 each has a size of several micrometers to several tens of micrometers and are arranged at intervals of several micrometers to several tens of micrometers.

For example, the diode array 110 may be fabricated in the same manner as a miniature fluorescence sensor including a single or multi-pixel architecture. The miniature fluorescence sensor may be configured to include a light source such as an LED or a laser, a photodetector adjacent to the light source, and a fluorescence emission filter.

For example, the diode array 110 may be configured to include a vertical cavity surface-emitting laser (VCSEL). The VCSEL is suitable for use in an integrated device because the VCSEL is capable of emitting light in a direction perpendicular to a semiconductor wafer plane (e.g., an upward direction). Compared to an LED, the VCSEL may emit the light with higher intensity and have an advantage of being implemented with a smaller size sensor. In addition, the VCSEL integrates various light sources to easily implement an integrated device.

In this case, it is difficult to accurately detect the alcohol concentration in the target F when the light emitted from the light emitting diodes 111a and 111b is not reflected from the target F but is directly incident on the photodiodes 112. Thus, the lens array 120 is used to reduce or minimize the interference between the light emitting diodes 111a and 111b and the photodiodes 112, which are arranged at the intervals of the micro units.

Meanwhile, the diode array 110 and the lens array 120 may be configured as one package. The optical alcohol detector 100 may be provided as a structure of a light transmitter receiver chip in which the diode array 110 and the lens array 120 are configured in one package. Thus, according to the present disclosure, it is possible to simplify a manufacture of the optical alcohol detector 100 and to prevent an arrangement of the light emitting diodes 111a and 111b and the photodiodes 112 from being dislocated in a manufacturing process of the optical alcohol detector 100.

The optical alcohol detector 100 may further include a substrate 140 where the diode array 110 and the controller 130 are disposed.

Referring to FIG. 2, the substrate 140 may be configured to include a first region 141 and a second region 142 having a lower thermal conductivity than the first region 141.

The diode array 110 may be disposed at the first region 141 of the substrate 140 and the controller 130 may be disposed at the second region 142 of the substrate 140. The diode array 110 includes the light emitting diodes 111a and 111b and the light emitting diodes 111a and 111b may generate heat when emitting the light. The light emitting diodes 111a and 111b and the photodiodes 112 constituting the diode array 110, and conductive wires electrically connecting the light emitting diodes 111a and 111b to the photodiodes 112 may be damaged when a temperature of the diode array 110 increases due to the heat generated in the diode array 110. Therefore, it is desired to effectively dissipate heat generated from the diode array 110.

According to one form, the heat may be effectively radiated through the substrate 140 because the diode array 110 is disposed at the first region 141 having a high thermal transfer rate (or a thermal conductivity) of the substrate 140.

The optical alcohol detector 100 may further include a cooler 150 for effective heat dissipation of the diode array 110 and the controller 130.

The cooler 150 may be disposed on the other side opposite to one side, where the diode array 110 and the controller 130 are disposed, to cool the substrate 140.

In another form, the cooler 150 may be configured as an air-cooled or oil-cooled cooler. Further, for example, the cooler 150 may be formed of a material having a high thermal conductivity such as metal, and may cool the substrate 140 with air. Alternatively, the cooler 150 may be formed of a material having a high thermal conductivity, a side of the cooler 150 which is not in contact with the substrate 140 may be in contact with a separate member, and therefore the substrate 140 may be cooled by transferring the heat to the separate member.

The optical alcohol detector 100 according to the present disclosure may be easily applied to anywhere near a driver's seat in addition to the start button inside the vehicle because the optical alcohol detector 100 has a vertical thickness T1 less than about 10 mm, which is a distance between an upper surface of the optical alcohol detector 100 and a lower surface of the optical alcohol detector 100.

Referring to FIG. 3, the plurality of light emitting diodes 111a and 111b includes at least one first light emitting diode 111a which emits light L1 of a first wavelength and at least one second light emitting diode 111b which emits light L2 of a second wavelength longer than the first wavelength.

At least one first light emitting diode 111a may include a plurality of first light emitting diodes 111a arranged in a predetermined column direction D1 to form a first light emitting diode column.

The second light emitting diodes 111b may include a plurality of second light emitting diodes 111b arranged in the column direction D1 to form a second light emitting diode column.

The plurality of photodiodes 112 may include a plurality of photodiodes 112 arranged in the column direction D1 to form a first photodiode column.

In one form, the plurality of photodiodes 112 may be arranged in a plurality of columns. Referring to FIG. 3, the plurality of photodiodes 112 may be arranged where a first photodiode column, a second photodiode column, and a third photodiode column are arranged in a row direction D2.

The diode array 110 may be configured to be arranged where the first light emitting diode column, the first photodiode column, and the second light emitting diode column are arranged in a row direction in order.

Alternatively, the diode array 110 may be configured to be arranged where the first light emitting diode column and the second light emitting diode column are alternately arranged between the plurality of first photodiode columns.

Through the above arrangement, the light which is reflected by the target F after being emitted from the first light emitting diode 111a and the light which is reflected by the target F after being emitted from the second light emitting diode 111b may be effectively detected by the photodiodes 112.

The first light emitting diode 111a may be a laser diode emitting laser beam of a first wavelength and the second light emitting diode 111b may be a laser diode emitting laser beam of a second wavelength.

According to the present disclosure, a difference in transmission and reception sensitivity of each wavelength due to a difference in a position of each laser diode may be reduced or minimized because the laser diodes emitting the laser beams of the different wavelengths are alternately arranged and the photodiodes are disposed between the laser diodes. Accordingly, alcohol (concentration) detecting performance may be improved.

Meanwhile, although not shown, the plurality of light emitting diodes 111a and 111b may further include a light emitting diode which emits light of a different wavelength in addition to the first wavelength and the second wavelength. In this case, the first light emitting diode column, the second light emitting diode column, and a third light emitting diode column may be arranged side by side in the row direction and the photodiode columns may be arranged therebetween in the same manner as described above.

The plurality of light emitting diodes 111a and 111b and the plurality of photodiodes 112 may be prepared to have a size of several micrometers (μm) to several tens of micrometers (μm), respectively.

The plurality of light emitting diodes 111a and 111b and the plurality of photodiodes 112 may be arranged as described above at the intervals of several micrometers (μm) to several tens of micrometers (μm) apart from each other.

According to the present disclosure, the light emitted from the plurality of light emitting diodes 111a and 111b may be directly irradiated toward the target F and the light reflected from the target F may be directly incident on the plurality of photodiodes 112. Therefore, light loss may be minimized in a process in which the light emitted from the light emitting diodes 111a and 111b is reflected by the target F and is received by the photodiodes 112, and alcohol (concentration) in the target F may be detected accurately.

On the other hand, conventionally it has been necessary to generate stronger light in the light emitter in consideration of light loss when the light generated in the light emitter is transmitted through an optical fiber or the like. However, according to the present disclosure, because such light loss may be reduced, relatively weak light may be used. Accordingly, intensity of the light generated in the light emitter may be lowered than that of the conventional emitter, and therefore the heat generated by the light may be reduced.

Referring to FIGS. 3 and 4, the lens array 120 may include a plurality of microlenses 121, which has a quantity corresponding to the number of the plurality of light emitting diodes 111a and 111b and the plurality of photodiodes 112 and are arranged corresponding to arrangement of the plurality of light emitting diodes 111a and 111b and the plurality of photodiodes 112.

In one form, the lens array 120 may include a plurality of microlenses 121 and a plate for fixing the plurality of microlenses 121.

In another form, the lens array 120 may be provided with a plurality of convex lens-shaped protrusions on one side of a plate-shaped base plate, and the plurality of microlenses 121 may be the protrusions described above. Here, the plate-shaped base plate and the convex lens-shaped protrusions (i.e., the microlenses) may be formed of a light-transmitting material.

Each of the plurality of microlenses 121 may have a convex shape toward the other side opposite to one side facing the plurality of light emitting diodes 111a and 111b and the plurality of photodiodes 112.

Referring to FIG. 4, for converging the light emitted from the plurality of light emitting diodes 111a and 111b and the light incident on the plurality of photodiodes 112, the plurality of microlenses 121 may be arranged to correspond to positions of the plurality of light emitting diodes 111a and 111b and the plurality of photodiodes 112 with respect to a vertical direction.

In other form, the first light emitting diode 111a and the second light emitting diode 111b may be provided with surface emitting laser diodes which emit laser beams at one surface thereof, respectively.

The light L1 of the first wavelength emitted from the first light emitting diode 111a and the light L2 of the second wavelength emitted from the second light emitting diode 111b may be refracted by the microlenses 121 to be convergingly irradiated toward the target F. To this end, focal distances of the microlenses 121 disposed at positions corresponding to the first light emitting diode 111a and the second light emitting diode 111b may be determined based on a position of the target F (e.g., a position at which the finger, that is, the target F, touches the button window 11 in FIG. 1).

The light which is incident on the photodiodes 112 after being reflected by the target F may be refracted by the microlenses 112 to converge on the photodiodes 112. The focal distances of the microlenses 121 disposed corresponding to the photodiodes 112 may be determined based on the thickness of the photodiodes 112 and the lens array 120 or a distance between the microlenses 121 and a detecting portion of the photodiodes 112.

Therefore, the microlenses 121 disposed corresponding to the first light emitting diode 111a and the second light emitting diode 111b and the microlenses 121 disposed corresponding to the photodiodes 112 may be provided with the same or different focal distance. In addition, the focal distances of the microlenses 121 may be determined depending on a structure of the object (the button 10 in one form) on which the optical alcohol detector 100 is installed.

Figure 5:
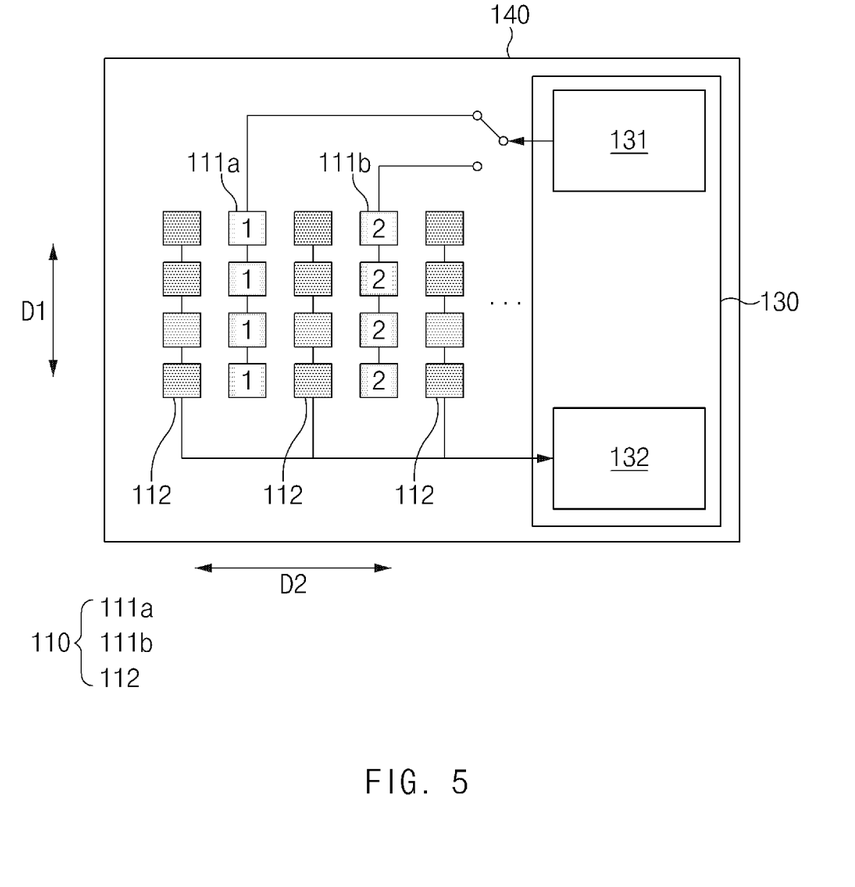
FIG. 5 illustrates a circuit of an optical alcohol detector.

FIG. 5 illustrates a circuit of an optical alcohol detector according to another form of the present disclosure.

The controller 130 may include a light emitting diode control circuit 131 for generating a signal for controlling the first light emitting diode 111a and the second light emitting diode 111b, and a photodiode output circuit 132 for receiving a signal generated in the photodiodes 112.

The controller 130 may detect the amount of alcohol (or the concentration of alcohol) based on the signal generated at the plurality of photodiodes 112 when the first light emitting diode 111a is turned on and the second light emitting diode 111b is turned off, and the signal generated at the plurality of photodiodes 112 when the first light emitting diode 111a is turned off and the second light emitting diode 111b is turned on.

More specifically, the controller 130 may determine the amount of alcohol in the target F by a following procedure.

First, the controller 130 turns on the first light emitting diode 111a to irradiate the light to the target F. The photodiodes 112 outputs a current corresponding to an optical signal to the controller 130 when the photodiodes 112 receives the light which is reflected by the target F after being emitted from the first light emitting diode 111a.

The controller 130 performs signal processing on the signal (e.g., an output current) received from the photodiodes 112 to quantitatively calculate an absorption rate of alcohol based on the light L1 of the first wavelength. That is, the controller 130 calculates the amount of light L1 of the first wavelength absorbed by alcohol in the target F.

In sequence, the controller 130 turns off the first light emitting diode 111a, and then turns on the second light emitting diode 111b to irradiate light to the target F. The photodiodes 112 outputs a current corresponding to an optical signal to the controller 130 when the photodiodes 112 receives the light which is reflected by the target F after being emitted from the second light emitting diode 111b.

The controller 130 performs signal processing on the signal (e.g., an output current) received from the photodiodes 112 to quantitatively calculate an absorption rate of alcohol based on the light L2 of the second wavelength. That is, the controller 130 calculates the amount of light L2 of the second wavelength absorbed by alcohol in the target F.

In sequence, the controller 130 estimates a variation of the absorption rate of alcohol with respect to the light of each wavelength to determine the amount of alcohol of the target F or the alcohol concentration of the target F.

The non-invasive optical alcohol detector according to exemplary forms, which are provided as described above, may be miniaturized in size compared to the conventional optical alcohol detector and may be applied to any part of the interior of the vehicle such as the start button of the vehicle. In addition, the optical alcohol detector may be installed in the vehicle to prevent a drinker from starting the engine, thereby preventing drunk driving.

According to the forms of the present disclosure, one or more of the following effects may be obtained.

First, the optical internal substance detector may be integrated to be miniaturized because the diode array including the plurality of light emitting diodes and the plurality of photodiodes, which each has the size of the micro unit and are arranged at intervals of micro units, is provided.

Second, the interference between the integrated light emitting diodes and the photodiodes may be prevented and the performance of the internal substance detector may be improved because the lens array disposed at the one side of the diode array is provided to converge the light emitted from the plurality of light emitting diodes and the light incident on the plurality of photodiodes.

The effects of the present disclosure are not limited to the effects mentioned above, and other effects not mentioned may be clearly understood by those skilled in the art from the description of the claims.

Hereinabove, although the present disclosure has been described with reference to exemplary forms and the accompanying drawings, the present disclosure is not limited thereto, but may be variously modified and altered by those skilled in the art to which the present disclosure pertains without departing from the spirit and scope of the present disclosure.

What is claimed is:

1. A non-invasive optical internal substance detector comprising:
    a diode array including:
        a plurality of light emitting diodes configured to emit light toward a target including an internal substance to be detected, and
        a plurality of photodiodes configured to receive light reflected from the target after being emitted from the plurality of light emitting diodes;
    a controller configured to control light emitting diodes of the plurality of light emitting diodes to be turned on or off and to process a signal obtained from photodiodes of the plurality of photodiodes; and
    a substrate in which the diode array and the controller are disposed,
    wherein the plurality of light emitting diodes and the plurality of photodiodes each have a size of several micrometers to several tens of micrometers and are arranged at intervals of several micrometers to several tens of micrometers from each other,
    wherein the substrate includes a first region and a second region having a lower thermal conductivity than the first region, and
    wherein the diode array is disposed at the first region of the substrate and the controller is disposed at the second region.

2. The non-invasive optical internal substance detector of claim 1, wherein the plurality of light emitting diodes includes:
    a first light emitting diode configured to emit light having a first wavelength, and
    a second light emitting diode configured to emit light having a second wavelength longer than the first wavelength.

3. The non-invasive optical internal substance detector of claim 2, wherein the controller is configured to detect an amount of the internal substance in the target based on a signal generated at the plurality of photodiodes when the first light emitting diode is turned on and the second light emitting diode is turned off, or a signal generated at the plurality of photodiodes when the first light emitting diode is turned off and the second light emitting diode is turned on.

4. The non-invasive optical internal substance detector of claim 1, wherein light emitting diodes of the plurality of light emitting diodes are divided into a first light emitting diode group including first light emitting diodes arranged in a predetermined column direction to form a first light emitting diode column, and a second light emitting diode group including second light emitting diodes arranged in the predetermined column direction to form a second light emitting diode column,
    wherein photodiodes of the plurality of photodiodes are arranged in the predetermined column direction to form a first photodiode column, and
    wherein a light wavelength emitted from the first light emitting diodes are different from a light wavelength emitted from the second light emitting diodes, and the first photodiode column is alternatively arranged with at least one of the first light emitting diode column or the second light emitting diode column.

5. The non-invasive optical internal substance detector of claim 4, wherein the first photodiode column is arranged between the first light emitting diode column and the second light emitting diode column.

6. The non-invasive optical internal substance detector of claim 4, wherein photodiodes of the plurality of photodiodes are arranged in the predetermined column direction to form a second photodiode column, and the first light emitting diode column and the second light emitting diode column are arranged alternately between the first and second photodiode columns.

7. The non-invasive optical internal substance detector of claim 1, further comprising:
    a lens array disposed at one side of the diode array and configured to converge the light emitted from the plurality of light emitting diodes and light incident on the plurality of photodiodes.

8. The non-invasive optical internal substance detector of claim 7, wherein the lens array includes a plurality of microlenses, and a number of microlenses of the plurality of microlenses is determined based on a number of light emitting diodes of the plurality of light emitting diodes and a number of photodiodes of the plurality of photodiodes, such that the microlenses respectively cover corresponding light emitting diodes or photodiodes.

9. The non-invasive optical internal substance detector of claim 8, wherein each of the plurality of microlenses has a convex shape toward other side opposite to one side facing the plurality of light emitting diodes and the plurality of photodiodes.

10. The non-invasive optical internal substance detector of claim 1, further comprising:
    a cooler configured to cool the substrate and disposed on other side opposite to one side of the substrate, where the diode array and the controller are disposed.

11. A non-invasive optical internal substance detector comprising:
    a diode array including:
        a plurality of light emitting diodes configured to emit light toward a target including an internal substance to be detected, and
        a plurality of photodiodes configured to receive light reflected from the target after being emitted from the plurality of light emitting diodes;
    a lens array disposed at one side of the diode array and configured to converge the light emitted from the plurality of light emitting diodes and light incident on the plurality of photodiodes;

a controller configured to control light emitting diodes of the plurality of light emitting diodes to be turned on or off and to process a signal obtained from photodiodes of the plurality of photodiodes; and a substrate in which the diode array and the controller are disposed, wherein the substrate includes a first region and a second region having a lower thermal conductivity than the first region, and wherein the diode array is disposed at the first region of the substrate and the controller is disposed at the second region.

* * * * *